United States Patent [19]
Corey et al.

[11] Patent Number: 6,022,548
[45] Date of Patent: Feb. 8, 2000

[54] COSMETIC SKIN CONDITIONING COMPOSITIONS CONTAINING METHOXYCINNAMYLOXY SALICYLATE

[75] Inventors: Joseph Michael Corey, Waterbury, Conn.; Victor DeFlorio, Cranford, N.J.; Anthony Vargas, Monroe, Conn.

[73] Assignee: Elizabeth Arden Co., New York, N.Y.

[21] Appl. No.: 09/048,738

[22] Filed: Mar. 26, 1998

[51] Int. Cl.[7] .............................. A61K 6/00; A61K 7/42; A61K 7/06
[52] U.S. Cl. ........................... 424/401; 424/59; 424/70.8
[58] Field of Search .................................. 424/70.8, 401, 424/59

[56] References Cited

U.S. PATENT DOCUMENTS

| | | |
|---|---|---|
| 2,116,347 | 5/1938 | Grether et al. |
| 5,262,407 | 11/1993 | Leveque et al. ........................ 514/159 |

FOREIGN PATENT DOCUMENTS

| | | |
|---|---|---|
| 0676194 | 11/1995 | European Pat. Off. |
| 93/10755 | 6/1993 | WIPO |

OTHER PUBLICATIONS

Abstract of JP 4036238, Feb.6, 1992.
E. Graf, "Anti–oxidant Potential Ferulic Acid," Free Radical Biology and Medicine, vol. 13, pp. 435–448, 1992.

*Primary Examiner*—Thurman K. Page
*Assistant Examiner*—Alysia Berman
*Attorney, Agent, or Firm*—Rimma Mitelman

[57] ABSTRACT

Cosmetic skin conditioning compositions containing ferulyl salicylate. The inventive compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

6 Claims, No Drawings

COSMETIC SKIN CONDITIONING COMPOSITIONS CONTAINING METHOXYCINNAMYLOXY SALICYLATE

FIELD OF THE INVENTION

Cosmetic methods and compositions for conditioning human skin by topical application to the skin of cosmetic compositions containing methoxycinnamyloxysalicylate.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. Consumers also frequently seek other benefits in addition to anti-aging.

A frequent, undesirable skin condition is "oily skin," the condition which results from the excessive amount of sebum on the skin. Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups.

Formation of free radicals in the skin does not appear to be related to the sebum secretion. Low levels of free radicals are formed in the skin as part of the natural metabolic pathways. The level of free radicals is increased in response to UV radiation and other environmental oxidants, e.g. pollution and cigarette smoke. Increased concentration of free radicals leads to lipid peroxidation in skin cells and cellular damage, which in turn results in a premature ageing of the skin with an accompanying loss of firmness and elasticity, wrinkles, discoloration, age spots, and dryness. Antioxidants, such as vitamin E (alpha-tocopherol), decrease the level of free radicals in the skin.

Cosmetic actives which provide more than one benefit are highly desirable, both from the manufacturer's and consumer's perspective. Especially valuable are compounds which are able to provide more than two cosmetic benefits.

U.S. Pat. No. 2,116,347 (Grether et al.) describes salicyloxy carboxy acid esters for external treatment of rheumatism. The Grether compounds differ from methoxycinnamyloxysalicylate employed herein at least in that the Grether compounds contain an ester group in place of a terminal carboxy group. Thus, the Grether compounds contain two ester bonds, whereas the compounds included in the present invention contain only one ester bond. Furthermore, the Grether compounds are aliphatic esters of salicylic acid, whereas the present ester is with an aromatic compound, methoxy cinnamic acid.

PCT application WO 93/10755 reports salicylic acid as an effective anti-wrinkling agent. Leveque et al. (U.S. Pat. No. 5,262,407) reports use of certain ring acylated salicylic acid derivatives as a treatment against skin aging. Ring alkylated salicylic acid has been reported in Japanese Patent 4036238 (Takasago Perfumery KK) for treatment of acne vulgaris. European Patent Application 0676194 (Roussel Uclaf) discloses cosmetic compositions for treatment of skin aging problems, the compositions containing salicylic acid or esters thereof. Salicylic acid esters disclosed in EP0676194 are non-ring esterified salicylic acid ester, i.e. salicylic acid is covalently bound via an ester bond to an alkyl chain or isopropylbenzyl.

E. Graf, "Anti-oxidant Potential of Ferulic Acid," Free Radical Biology and medicine, vol. 13, pp. 435–48, 1992 discloses that ferulic acid may photoprotect the skin when used in cosmetic lotions.

None of the art described above discloses methoxycinnamyloxy salicylate included in the present invention. Methoxycinnamyloxy salicylate is salicylic acid covalently bound via an ester bond to methoxycinnamic acid (a.k.a. ferulic acid). Methoxycinnamyloxy salicylate may also be called "ferulyl salicylate." It has been found, as part of the present invention that an ferulic acid or salicylic acid when employed individually do not significantly reduce sebum secretion, whereas ferulyl salicylate employed in the present invention attains significant reduction in sebum secretion. Furthermore, the use of ferulyl salicylate is advantageous compared to using a physical mixture of salicylic acid and ferulic acid: ferulyl salicylate is easier to formulate with, since ferulic acid and salicylic acid individually carry a greater number of incompatibilities than a single molecule of ferulyl salicylate.

SUMMARY OF THE INVENTION

The present invention includes a skin conditioning composition comprising:

(a) from 0.0001 to 20 wt. % of methoxycinnamyloxy salicylate of Formula I:

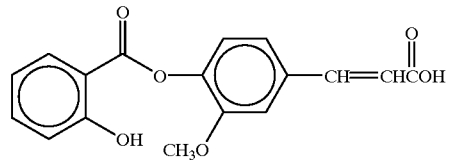

and (b) a cosmetically acceptable vehicle.

The present invention also includes a method of controlling or preventing an oily skin condition, especially in the facial area, by applying to the skin a composition comprising methoxycinnamyloxy salicylate in a cosmetically acceptable vehicle.

The invention also includes a cosmetic method of reducing, preventing or controlling sebum secretion from sebocytes by applying the inventive composition to the skin.

The invention also includes a cosmetic method of stimulating collagen and glycosaminoglycan synthesis by fibroblasts in the skin, by applying the inventive composition to the skin.

The invention also includes a cosmetic method of protecting the skin from free radical activity (i.e., relieving the oxidative stress in the skin) by applying to the skin the inventive composition.

The invention also includes a cosmetic method of treating or delaying chronoaged, photoaged, dry, lined or wrinkled skin, shielding the skin from harmful UVA and UVB light (sunscreening), increasing stratum corneum firmness and flexibility, and generally increasing the quality of skin by applying to the skin the inventive composition.

The inventive methods and compositions provide control of sebum secretion from sebocytes, improved oil control and improved skin feel, prevent shine and stickiness, while also providing anti-oxidant and anti-aging benefits which results in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, hands and scalp.

Methoxycinnamyloxysalicylate is of Formula I:

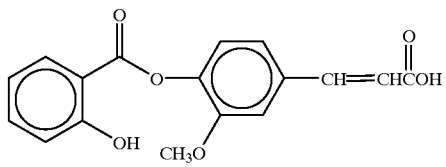

The terms "methoxycinnamyloxysalicylate" and "ferulyl salicylate" are used interchangeably herein.

(a) preparing a salicylic acid h alide by reacting salicylic acid with thionyl halide o r oxalyl halide; and
(b) reacting the salicylic acid halide with ferulic acid, to obtain the inventive compound of Formula I:

In the first step, salicylic acid is mixed with thionyl (or oxalyl) halide, most preferably chloride, (molar ratio in the general range of from 1:1 to 2:1) in an anhydrous, typically non-polar, solvent, in the presence of pyridine catalyst, at a temperature of from 20 to 45° C. for 0.5–2 hours. At the end of this reaction, salicylic acid chloride id obtained. Optionally, the solvent is distilled at least partially.

Subsequently, ferulic acid is dissolved in a dry solvent (e.g. dry acetone, toluene, THF) and pyridine is added to this solution (1 equivalent per 1 equivalent of salicylic acid halide). Salicylic acid chloride is added dropwise, with stirring, to this solution. The molar ratio of salicylic acid chloride to ferulic acid is typically in the range of from 1:1 to 1:2. The reaction is conducted typically 40–45° C. for several hours, before being heated to reflux for 3 hours, and the completion is monitored by TLC.

Subsequently, the solvent is removed and the product is isolated by extraction and purified by column chromatography and recrystallization. The product is a white powder.

Methoxycinnamyloxy salicylate is incorporated in the inventive compositions in an amount of from 0.0001 to 20%, preferably in order to maximize benefits at a minimum cost, in an amount of from 0.01 to 12%, most preferably from 0.1 to 8%.

Cosmetically Acceptable Vehicle

The composition according to the invention also comprises a cosmetically acceptable vehicle to act as a dilutant, dispersant or carrier for methoxycinnamyloxy salicylate in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 1 0,000,000 mm²/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, the amount of water is at least 50 wt. % of the inventive composition, most preferably from 60 to 80 wt. %, by weight of the composition. The preferred compositions are oil-in-water emulsions, containing at least 60%, preferably at least 80% water.

Optional Skin Benefit Materials and Cosmetic Adjuncts

Although methoxycinnamyloxysalicylate has a sunscreen functionality (because it is a salicylate derivative), the inventive compositions preferably include additional sunscreens to further lower skin's exposure to harmful UV rays.

Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triusopropyl trilinoleate and trilauryl citrate. Acceptable straight chain fatty esters include lauryl palmitate, myristyl lactate, oleyl eurcate and stearyl oleate. Preferred esters include cococaprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicone-based anhydrous composition within a gelatine capsule), incorporated by reference herein. The invention accordingly also provides a closed container containing a cosmetically acceptable composition as herein defined.

The following specific examples further illustrate the invention, but the invention is not limited thereto.

EXAMPLE 1

This example illustrates synthesis of methoxycinnamyloxysalicylate, a compound included in the inventive compositions.

Methods and Materials

Proton magnetic resonance spectra were recorded on a Bruker AC 200 model spectrophotometer. Chemical shifts are reported in parts per million from teramethylsilane as an internal standard. Spin multiplicities are indicated as follows: s (singlet), d (doublet), t (triplet), q (quartet), m (multiplet) and br (broad). The deuterated NMR solvents contain 99.0–99.8% deuterium in the indicated position, and were purchased from Cambridge Isotopic Laboratories.

Gas chromatography (GC) was performed using a Hewlett-Packard 5890 Series II gas chromatograph with an HP 7673 injector controlled by the Hewlett-Packard ChemStation software. The Hewlett-Packard HP-1 column used was 25 M×0.22 mm with a 0.33 um coating of cross-linked methyl silicone . The parameters were as follows:

Inj. temp.=290° C., det. temp.=290° C., initial oven temp.=50° C., initial time=5 min., rate=25° C./min., final oven temp.=290° C. Samples were analyzed as trimethyl silyl ethers/esters.

Gas chromatography/mass spectrometry was performed on a Hewlett-Packard 5890 Series II gas chromatograph in conjunction with a Finnigan MAT ITD 800 ion trap detector. The 25 M×0.32 mm HP-5 column had a 0.52 um coating of 5% cross-linked phenyl methyl silicone.

Differential Scanning Calorimetry experiments were run on a Dupont DSC with a 2910 cell base and a 2100 thermal analyst. Samples of approximately 1 mg were accurately weighed into aluminum pans which were than hermetically sealed. After equilibration at 30° C., the samples were heated at a rate of 5° C./minute.

All solvents were reagent grade and were used as received. All reagents were purchased from the Aldrich or Sigma Chemical Companies and were used as received.
Step 1:

Into a clean, dry 250 mL round bottomed flask were charged 5.0 g (36 mmoles) of salicylic acid, 100 mLs of anhydrous toluene and 4–5 drops of pyridine catalyst. The flask was equipped with a stir bar, addition funnel and nitrogen bubbler. Into the addition funnel were charged 4.7g (40 mmoles) of thionyl chloride in 20–25 mLs of anhydrous toluene. The thionyl chloride solution was added to the reaction flask dropwise under ambient conditions. When the addition was complete, the reaction stirred at 40–45° C. for several hours before any excess thionyl chloride and some of the toluene were removed under vacuum.
Step 2:

Into a clean, dry 500 mL round bottomed flask were charged 7.0 g (36 mmoles) of ferulic acid, 200 mLs of anhydrous toluene and 3.4 g (40 mmoles) of pyridine. The flask was equipped with a stir bar, addition funnel and nitrogen bubbler. Into the addition funnel was added the salicyloyl chloride solution. The salicyloyl chloride solution was added to the reaction flask dropwise under ambient conditions. When the addition was complete, the reaction stirred at 40–45° C. for several hours before being heated to reflux for 3 hours before the heat was removed and the reaction continued to stir under ambient conditions overnight.

The reaction mixture was filtered under vacuum to remove the brown precipitate formed during the reaction. The toluene filtrate was concentrated under vacuum to yield 5.2 g of yellow solid which was 52% methoxycinnamyloxy salicylate by gas chromatography and gas chromatography/mass spectrometry. 2.4 g of product were purified by silica gel column chromatography to yield 600 mg of pure methoxycinnamyloxy salicylate (a.k.a. ferylyl salicylate) as a fine white powder.

$^1$H NMR (200 MHz, CdCl3): d 8.0 (d, 1 H), 7.6 (m, 2H), 7.0(m, 2H), 6.5 (d, 1 H), 3.9 (s, 3H); GC (Retention time): 15.9 minutes; DSC: Onset Temperature(° C.): 192; m/z (GC/MS): 531 (M+H)$^+$ $_{(3 \times TMS)}$.

EXAMPLE 2

This example measured production of procollogen I by fibroblasts in response to treatment with ferulyl salicylate ("FS").

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643; and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, N.Y. and used in passages 5–10. Cells were seeded at a density of approximately 10,000/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, the medium was removed and cells were washed with serum-free DMEM, and each well dosed with 200 $\mu$l of a solution of a test compound in serum-free DMEM. Each dosing was replicated in a total of six wells. Test compounds were used at concentrations indicated in Table 1 below. Control did not contain a test compound. After 24 hours, the test compound solution or the control solution was removed and cells redosed with 100$\mu$l of a solution of a test compound in serum-free DMEM. Test compounds were used at concentrations indicated in Table 1 below. After 24 hours, the test compound solution or the control solution was removed and stored over the weekend at 4° C. with protease inhibitor (Aprotinin from Sigma) in a ratio of aprotinin to media of 1:200. The test compound solution was then diluted in DMEM (approximately 20 $\mu$L sample in 200 $\mu$l DMEM).

Nitrocellulose membrane and 3 sheets of filter paper were soaked in TRIS buffered saline (TBS, pH 7.3.). BioRad slot blot apparatus (BioRad Labs, Calif.) was set up with 3 sheets filter paper on bottom, membrane on top, and tightened tightened. 100 ml TBS was added per well. Vacuum was used to suck TBS through membrane. The test compound solution or control was vortexed, then 100 $\mu$l was loaded per well and gravity filtered. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0. 1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was washed 3 times for 5 minutes in TBS/0.1% Tween. 3 mL PBS was incubated with 30 $\mu$l each of solutions A and B from Vectastain Kit for 30 minutes. The membrane was placed in the resulting solution for 30 minutes in a sealed bag with shaking. The membrane was then removed and washed twice for 5 minutes in TBS/ 0.1% Tween. The membrane was then stained using the following solution:

12.5 mg 3-amino 9-ethyl carbazole (Sigma); 3.125 (approximately) mL DMF (N,N- dimethylformamide, from Sigma); 21.5 mL 0.2M NaOAc buffer, pH 5.2; 12.5 $\mu$l $H_2O_2$.

The membrane was stained until color developed and the reaction stopped with 2 washes for 10 minutes in tap water. The blot was scanned on a Bio-Rad GS700 Image Analysis densitometer. Fold increase was calculated as a ratio of densitometer reading for cells treated with a test compound over control.

The results that were obtained are summarized in Table 1.

TABLE 1

| Test Compound (concentration) | Densitometer reading (avg) | Standard deviation | p-value (vs. control) | Fold increase over control |
|---|---|---|---|---|
| Control | 0.585 | 0.175 | | 1 |
| FS (0.01%) | 0.876 | 0.129 | 0.008 | 1.5 |
| FS (0.001%) | 1.03 | 0.0861 | 0.0002 | 1.8 |
| FS (0.0001%) | 1.07 | 0.193 | 0.001 | 1.8 |

It can be seen from the data in Table 1 that the addition of ferulyl salicylate at various concentrations to fibroblast cultures resulted in increased procollagen I production, as indicated by higher densitometer readings compared to control.

EXAMPLE 3

This example measures production of glycosaminoglycans by fibroblasts in response to treatment with various test compounds. Glycosaminoglycans (GAGs) are a family of polysaccharides which (with the exception of hyaluronic acid (HA)) can be linked to a protein core, forming a proteoglycan. The main GAGs in the dermis are HA and dermatan sulfate, with chondroitin-4-sulfate and chondroitin-6-sulfate present in small amounts. Made by both keratinocytes and dermal fibroblasts, GAGs are essential components of the extracellular matrix, although they make up only 0.2% of the dry weight of skin. GAGs hydrate the skin (HA can hold up to 1000× its mass in water) and maintain basement membrane integrity, regulate cellular interactions and nutrient transport, and are involved in collagen and possibly elastic fiber formation. The proportion of GAGs (especially HA) in the dermis has been shown to be diminished with aging. See Perlish et al, "The Role of Glycosaminoglycans in Aging of the Skin." Retinoic acid, the benchmark anti-aging active, has been shown to increase GAG content of the spinous and granular layers of the epidermis and the papillary dermis of aged skin in vivo. See Kligman et al., "Effects of topical tretinoin on non- sun-exposed protected skin of the elderly," J. Am Acad Dermatol 1 993;29:25–33.

Protocol for measuring GAGs

Neonatal human dermal fibroblasts were purchased from Clonetics Corp., San Diego, Calif. and used in passages 5–10. All materials for cell culture were purchased from Life Technologies, N.Y. Cells were seeded at a density of approximately 50,000/well in a 12-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, each well was rinsed in serum-free DMEM and the cells dosed with test compounds (in triplicate) in 750 $\mu$L of serum-free DMEM. Test compounds were used at a concentration indicated in Table 2 below. Controls did not contain any test compounds. After 24 hours, this medium was aspirated and the treatment step repeated. After a second 24-hour period, this medium, containing the soluble GAGs, was collected and frozen until analysis.

A positively-charged Zeta Probe membrane was soaked in sterile water and placed into the Dot-Blot Apparatus (both Bio-Rad Labs, Hercules, Calif.). 100 µL of water was applied to each well and pulled through using a vacuum. After thawing, 100 µL of test solution samples or standards (Hyaluronic acid or Chondroitin Sulfate from bovine trachea, Sigma, St. Louis, Mo.) was applied to the membrane and allowed to gravity filter (about 1.5–2 hours). GAGs were now bound to membrane. The membrane was blocked in 3% w/v fatty acid free bovine serum albumin (Sigma) in water for one hour. A dye solution of 0.5% w/v Alcian Blue dye (ICN Biochemicals, Cleveland, Ohio.) in 3% acetic acid, pH approximately 2.3, was made. The membrane was washed twice in distilled water and then stained in the dye solution on a rotary shaker for 15 minutes. The dye was poured off and the membrane destained twice for 15 minutes each time in 3% acetic acid. The membrane was rinsed in water and left to dry overnight. The Bio-Rad GS 700 Image Analysis Densitometer was used to quantitate the intensity of color in each spot. Fold increase over control was calculated as a ratio of densitometer reading for cells treated with a test compound over control.

The results that were obtained are summarized in Table 2.

TABLE 2

| Test Compound (concentration) | Densitometer reading (avg) | Standard Deviation | p-value (vs. control) | Fold increase over control |
|---|---|---|---|---|
| Control | 0.184 | 0.0394 | | 1 |
| FS (0.05%) | 0.126 | 0.0389 | 0.03 | 0.7 |
| FS (0.005%) | 0.228 | 0.118 | 0.4 | 1.2 |
| FS (0.0005%) | 0.272 | 0.0841 | 0.04 | 1.5 |

It can be seen from the data in Table 2 that the addition of ferulyl salicylate at various concentrations to fibroblast cultures resulted in increased GAGs production, as indicated by higher densitometer readings compared to control.

EXAMPLE 4

This example reports an in vitro analysis of sebum suppression by various test compounds.

In Vitro Sebocyte Lipogenesis Assay

Human sebaceous glands were isolated from the nose of a male (age 60) and cultured using submerged tissue culture techniques (Bajor et al, J. Invest. Dermatol. 102: 1994, P. 564). These sebocytes accumulate intracellular lipid droplets characteristic of mature human sebum. Ferrulic and salicylic acids were obtained from Sigma.

Harvested and passaged sebocytes were added to each well of a 48 well tissue culture plate and incubated at 37° C. in the presence of 7,5% $CO_2$ for 7 days. On the day of experimentation, the growth medium was removed and the sebocytes washed three times with Dulbecco's Modified Eagle's medium (DMEM; glucose free, phenol red free). Fresh DMEM in 0.5 ml amount was added to each well and 5 µl of a test agent, at final concentrations ranging from 1 micromolar to 1 millimolar. Triplicate wells were utilized for each sample. Controls consisted of DMEM, ethanol (used to solubilize methoxycinnamyloxy salicylate), and tridecylsalicylate, a positive control which decreases sebum production and was used as a control to verify the integrity of the sebocyte assay. All cultures were incubated at 37° C./7.5% $CO_2$ for 30 minutes. Radioactive label was prepared by adding 100 µl of $^{14}C$ labeled acetic acid (Amersham, sodium salt, specific activity of 56 mCi/mmol) to 10 ml of 25 mM sodium acetate buffer. Then, 50 µl was added to each well containing the sebocytes and test agents. The cultures were returned to the incubator for four hours. Thereafter, the sebocytes were rinsed three times with fresh phosphate buffered saline (PBS) to remove unbound active and radioactive label. Radioactive label remaining in the cultured sebocytes was counted using a Beckman scintillation counter. The results were expressed as % reduction compared to control (ethanol). The higher the number, the beeter the result.

The results that were obtained are summarized in Table 3 below.

TABLE 3

| Compound | Concentration | % Reduction in $^{14}C$ Label Incorporation | Standard Deviation | p value vs. control |
|---|---|---|---|---|
| | EXPERIMENT 1 | | | |
| FS | 1 micromolar | 17.8 | 4.6 | 0.065 |
| | 10 micromolar | 34.4 | 3.3 | 0.007 |
| | 100 micromolar | 30 | 8.8 | 0.022 |
| | 1 mM | 52.7 | 12.3 | 0.0055 |
| | EXPERIMENT 2 | | | |
| FS | 1 micromolar | 19.6 | 1.7 | 0.015 |
| | 10 micromolar | 28 | 5.1 | 0.0022 |
| | EXPERIMENT 3 | | | |
| Salicyclic Acid | 1 micromolar | 0.1 | 5.6 | 0.97 |
| | 10 micromolar | −2.8 | 3.4 | 0.283 |
| | 100 micromolar | −4.1 | 8.6 | 0.459 |
| | EXPERIMENT 4 | | | |
| Ferulic acid | 1 micromolar | 2.7 | 6.8 | 0.545 |
| | 10 micromolar | 4.1 | 6.2 | 0.33 |
| | 100 micromolar | 8.6 | 8.6 | 0.009 |

It can be seen from the results in Table 3 that at a concentration of 1 micromolar and higher ferulyl salicylate consistently suppressed sebum secretion by sebocytes. Ferulic acid was only barely statistically effective at the highest concentration of 100 micromolar. Salicylic acid was not effective.

EXAMPLE 5

This example reports a chemical assay of antioxidant activity of ferulyl salicylate.

Chemical assay measured the antioxidant activity of ferulyl salicylate tested at a concentration of 1M solution. 2,2'azino-di-(3-ethylbenzthialoine sulphonate) (6.1 µmol/l) and metmyoglobin (610 µmol/l) were solubolized in phosphate buffered saline (5 mmol/l, pH 7.4). 20µL of ferulyl salicylate was then added and absorbance was measured at 734 nm before and after addition of the substrate, hydrogen peroxide (250 µmol/l). The initial absorbance was subtracted from the substrate containing absorbance. This prevents discrepancies in absorbance due to the test compound itself. The absorbance changes with time, thus multiple time points were examined. Results were expressed as % oxidation relative to a control containing all assay components but etanal instead of test reagent (100% oxidation). A high number means no prevention of oxidation, a poor antioxidant. The antioxidant activity of Trolox (registered trademark of Hoffman-LaRoche), a water soluble form of vitamin E was measured to establish the validilty of the test. Trolox was purchased from Aldrich (2.5 mmol/l). Trolox % oxidation was calculated relative to water (100% oxidation). The lower the % oxidation values, the better is the anti-oxidant.

The results that were obtained are summarized in Table 4.

TABLE 4

| Compound | % oxidation at 3 minutes | % oxidation at 6 minutes | % oxidation at 9 minutes | % oxidation at 15 minutes |
|---|---|---|---|---|
| Trolox | −0.70 | 15.8 | 44.6 | — |
| FS | 1.3 | 0.83 | 0.37 | 0.2% |

It is evident from the results in Table 4 that ferulyl salicylate has excellent anti-oxidant activity, at both concentrations tested. The chemical assay outlined above measures antioxidant activity obtained via direct free radical quenching, not via antuinflammatory pathway. The assay establishes that ferulyl salicylate acts as an antioxidant via direct free radical quenching.

EXAMPLE 6

Example 6 illustrates topical compositions according to the present invention. The compositions can be processed in conventional manner. They are suitable for cosmetic use. In particular the compositions are suitable for application to wrinkled, rough, flaky, aged and/or UV-damaged skin and/or oily skin to improve the appearance and the feel thereof as well as for application to healthy skin to prevent or retard deterioration thereof.

| INGREDIENT | % w/w |
|---|---|
| OIL-IN-WATER EMULSION | |
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Ferulyl Salicylate | 8.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Ferulyl Salicylate | |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total → | 100.00 |
| WATER-IN-OIL EMULSION | |
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Ferulyl Salicylate | 5.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |
| HYDRO-GEL | |
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Ferulyl Salicylate | 1.00 |
| Methylparaben | 0.30 |
| Polysorbate 20 | 0.25 |
| Disodium EDTA | 0.10 |
| Germall II | 0.10 |
| Total → | 100.00 |
| ANHYDROUS SERUM | |
| Cyclomethicone | 72.40 |
| Ferulyl Salicylate | 5.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total → | 100.00 |
| HYDRO-ALCOHOL GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Ferulyl Salicylate | 1.00 |
| Methylparaben | 0.30 |
| Polysorbate 20 | 0.25 |
| Disodium EDTA | 0.10 |
| Germall II | 0.10 |
| Total → | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising:

(a) from 0.0001 to 20 wt. % of methoxycinnamyloxy salicylate of Formula 1:

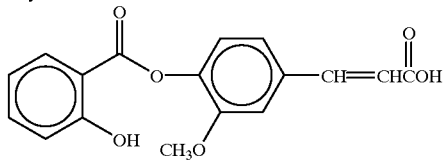

and (b) a cosmetically acceptable vehicle.

2. A method of controlling an oily skin the method comprising applying to the skin the composition according to claim 1.

3. A method of reducing or controlling sebum secretion from sebocytes in the skin, the method comprising applying to the skin the composition according to claim 1.

4. A method of stimulating collagen and glycosaminoglycan synthesis by fibroblasts in the skin, the method comprising applying to the skin the composition according to claim 1.

5. A method of treating aged, photoaged, dry, lined or wrinkled skin, the method comprising applying to the skin the composition according to claim 1.

6. A method of shielding the skin from harmful UVA and UVB light, the method comprising applying to the skin the composition according to claim 1.

* * * * *